(12) United States Patent
Huwiler et al.

(10) Patent No.: US 8,720,496 B2
(45) Date of Patent: May 13, 2014

(54) DEVICE, KIT, AND METHOD FOR FILLING A FLEXIBLE RESERVOIR CONTAINER IN A NEGATIVE PRESSURE CHAMBER

(75) Inventors: Christoph Huwiler, Baar (CH); Florian Kuehni, Wabern (CH); Gerald Studer, Flaach (CH); Martin Wyss, Burgdorf (CH); Ulrich Haueter, Grosshoechstetten (CH); David Teutsch, Schuepfen (CH)

(73) Assignee: Roche Diagnostics International AG, Rotkreuz (CH)

( * ) Notice: Subject to any disclaimer, the term of this patent is extended or adjusted under 35 U.S.C. 154(b) by 793 days.

(21) Appl. No.: 12/939,272

(22) Filed: Nov. 4, 2010

(65) Prior Publication Data

US 2011/0108158 A1 May 12, 2011

(30) Foreign Application Priority Data

Nov. 6, 2009 (EP) ..................................... 09175262

(51) Int. Cl.
*B65B 3/14* (2006.01)
(52) U.S. Cl.
CPC ....................................... *B65B 3/14* (2013.01)
USPC ................ 141/65; 141/114; 141/10; 604/131
(58) Field of Classification Search
CPC ............................................... B65B 3/10–3/14
USPC ............. 141/2, 7, 10, 18, 25–27, 59, 65, 114; 604/131, 408
See application file for complete search history.

(56) References Cited

U.S. PATENT DOCUMENTS

| | | | | |
|---|---|---|---|---|
| 3,965,946 A | * | 6/1976 | D'Alo | 141/51 |
| 4,817,687 A | * | 4/1989 | Lofgren et al. | 141/65 |
| 4,922,975 A | * | 5/1990 | Polaschegg | 141/104 |
| 5,437,201 A | * | 8/1995 | Krueger | 73/864.35 |
| 6,233,617 B1 | | 5/2001 | Rothwein et al. | |
| 6,623,455 B2 | * | 9/2003 | Small et al. | 604/131 |
| 7,254,237 B1 | | 8/2007 | Jacobson et al. | |
| 7,963,954 B2 | * | 6/2011 | Kavazov | 604/403 |
| 7,976,505 B2 | * | 7/2011 | Hines et al. | 604/180 |
| 2002/0087884 A1 | | 7/2002 | Shacham et al. | |
| 2003/0065918 A1 | | 4/2003 | Willey | |
| 2008/0269682 A1 | * | 10/2008 | Kavazov et al. | 604/126 |
| 2009/0163866 A1 | | 6/2009 | Hines et al. | |
| 2010/0094241 A1 | * | 4/2010 | Remde et al. | 604/403 |
| 2010/0234824 A1 | * | 9/2010 | Christoph et al. | 604/406 |
| 2011/0132490 A1 | * | 6/2011 | Kuhni et al. | 141/7 |
| 2011/0247719 A1 | * | 10/2011 | Kavazov | 141/1 |
| 2012/0150139 A1 | * | 6/2012 | Studer | 604/408 |

FOREIGN PATENT DOCUMENTS

| | | | |
|---|---|---|---|
| EP | 1 770 900 A1 | 4/2007 | |
| EP | 1 973 265 A1 | 9/2008 | |
| EP | 2179755 A1 | 4/2010 | |
| EP | 2193815 A1 | 6/2010 | |
| EP | 2229927 A1 | 9/2010 | |
| GB | 2 404 126 A | 1/2005 | |
| WO | 2004/017600 A1 | 2/2004 | |
| WO | 2008/154467 A1 | 12/2008 | |

\* cited by examiner

*Primary Examiner* — Timothy L Maust
*Assistant Examiner* — Robert Bell, III
(74) *Attorney, Agent, or Firm* — Dinsmore & Shohl LLP

(57) ABSTRACT

A device, kit, and method for transferring a liquid medicament from a supply container to a flexible reservoir container are disclosed. The device may comprise a compartment unit and an adapter unit. The compartment unit may have a sealingly closable chamber, arranged for housing the flexible reservoir container and for being fluidly connected with a pump mechanism. The adapter unit may have at least one transfer passage for transferring liquid from a supply container connected to the adapter unit to the flexible reservoir container, and a separator arranged in the transfer passage for separating gas bubbles from a liquid streaming through the transfer passage. The separator may be fluidly connected to the chamber.

20 Claims, 11 Drawing Sheets

FIG. 3C
FIG. 4
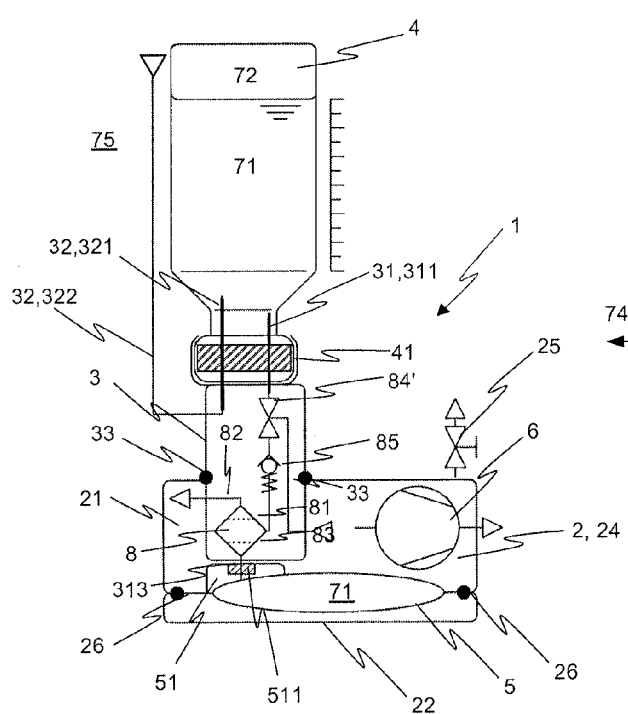
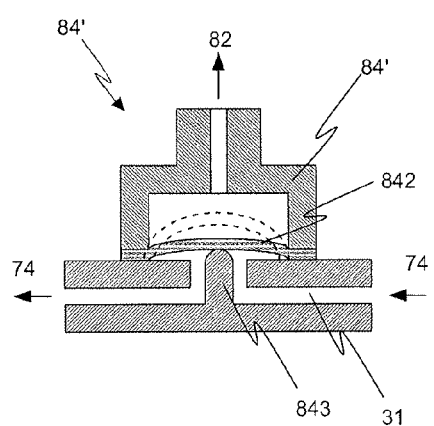

FIG. 8A
FIG. 8B
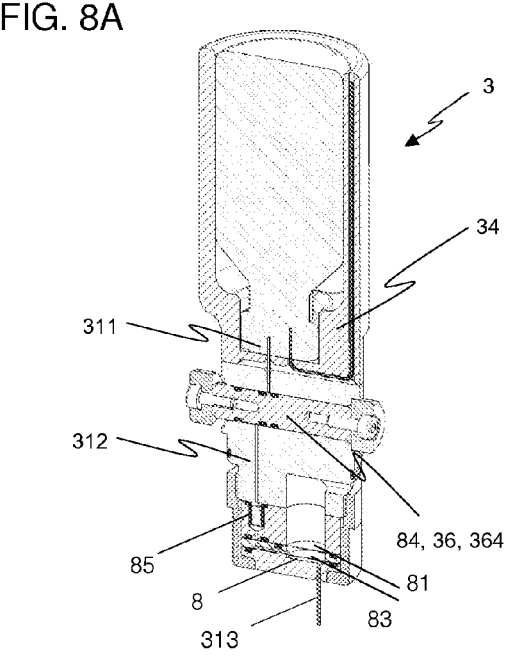
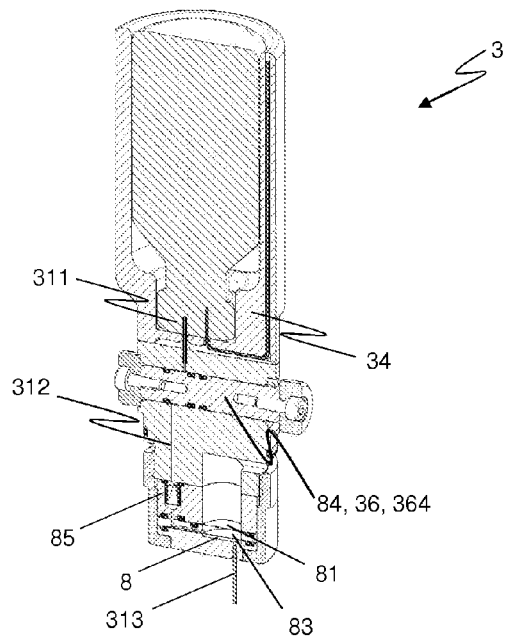

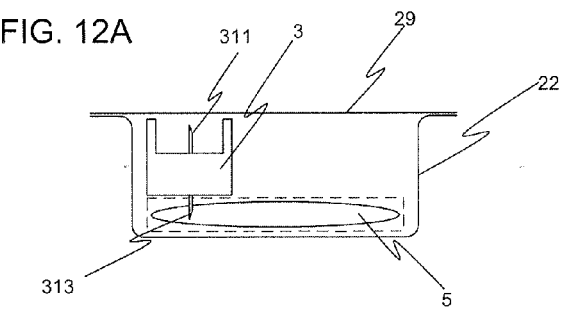
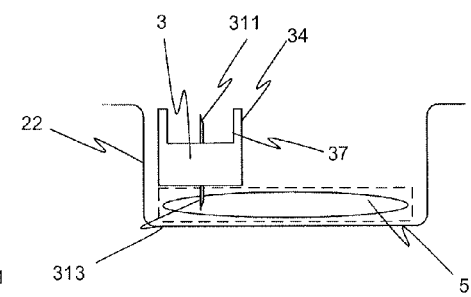
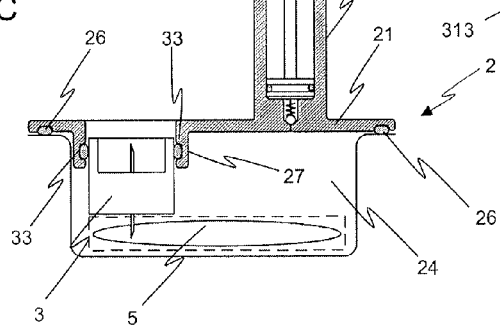
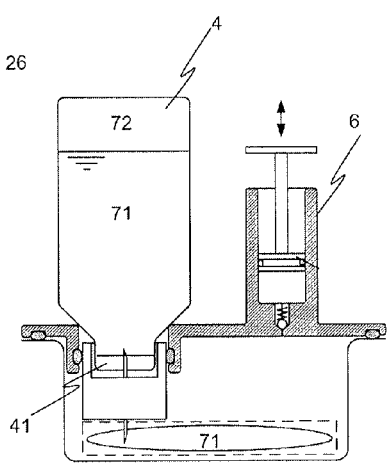
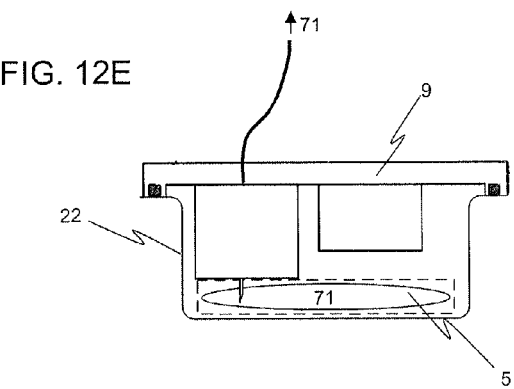

DEVICE, KIT, AND METHOD FOR FILLING A FLEXIBLE RESERVOIR CONTAINER IN A NEGATIVE PRESSURE CHAMBER

CROSS-REFERENCE TO RELATED APPLICATIONS

This application claims the benefit of priority under 35 U.S.C. §119 of European Application No. 09175262.6, filed Nov. 6, 2009.

TECHNICAL FIELD

The present application relates generally to transferring a liquid medicament from a supply container, and, in particular, to devices which transfer a liquid medicament from a supply container to a flexible reservoir container for use, e.g., in an infusion pump device, a kit with such a device, and methods thereof.

BACKGROUND

Devices for the automated release of liquid medicaments are normally used with patients who have a continuous and, in the course of the day, may have a varying need of a medicine that can be administered by subcutaneous infusion. Specific applications are, for example, certain pain therapies and the treatment of diabetes, in which computer controlled infusion pump devices are used, such as insulin pumps. Such devices can be carried by a patient on the body and contain a certain amount of liquid medicament in a medicine reservoir in the form of a container. The medicine reservoir often contains enough medicine for one or several days. The liquid medicament is supplied to the patient's body from the medicine reservoir by subcutaneous infusion of injection, through an infusion cannula or an injection needle.

As used herein, the terms "medicament" and "liquid medicament" are meant to encompass any drug-containing liquid medicine, or therapeutic or diagnostic liquid, capable of being passed through a delivery element such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In particular, the term medicament encompasses insulin preparations ready for administration.

The terms "subcutaneous infusion" and "subcutaneous injection" are meant to encompass any method in which a needle device is inserted at a selected site within the body of a patient for subcutaneous, intravenous, intramuscular or intradermal delivery of a liquid medicament to a subject. Further, the term needle defines a piercing member (including an array of micro needles) adapted to be introduced into or through the skin of a subject.

Particularly in self-administration of liquid medicaments, patients using the medicament and administering it desire convenience and discretion. As a consequence, the dimensions of such infusion devices are limited. However, the overall length, width and thickness should be as small as possible to remain hidden under clothing and to be comfortably carried.

While there are fully or partly disposable single-use infusion pump devices, such devices are typically non-disposable and are loaded with a disposable drug cartridge. Disposable cartridges are preferable for sterility and contamination prevention reasons. They may be delivered pre-filled with a certain liquid medicament, or empty, ready to be filled by a user. The self-filling of containers has the advantage that medicaments that are not readily available in pre-filled containers can be used for such infusion pump devices, thereby providing the patient with a larger choice of sources for his medicaments. Furthermore, the stability of many medicaments in liquid form, particularly in plastic containers, can only be guaranteed by the manufacturer for a certain amount of time.

The standard infusion pump devices that are carried on or near the body have a medicine reservoir with a cylindrical ampoule and a displacement piston, which is pushed into the ampoule by a piston rod or threaded spindle in order to convey the liquid medicament. These known designs have the disadvantage of being longer and/or thicker than desired, therefore, the resulting dimensions are not adequate for compact infusion pumps.

To reduce the overall volume of an infusion pump device, the syringe-type dosing mechanism can be replaced by a downstream pump system. In such a device, a miniaturized pump is arranged downstream of the main reservoir and causes a suction pressure that conveys the product from the reservoir to its destination. The reservoir in this type of an infusion pump device is realized as a flexible container. Such a flexible container may, for example, have the form of two flexible wall sheets that are sealed together. Flexible containers have the advantage of a smaller volume surplus of the container in relation to its content, which reduces the manufacture costs and the achievable dimensions of an infusion pump device using such a flexible container. The volume of a flexible container for use in an infusion pump device may be up to 10 ml, for example. A typical range for diabetes therapy is 1.5 to 3.5 ml. For other therapies, e.g. pain therapy, that use other administration regimes, other volume ranges may be more preferable.

A common problem of flexible containers, as they are known, is air remaining in the container. If, for example, a flexible container is empty and is filled with the appropriate liquid medicament by the user himself, there may be a certain amount of air in the container after the filling process. If the air remains in the container or in the fluidic system of a pump system, air bubbles may be administered instead of the liquid medicament, which leads to potentially dangerous dosing errors. Furthermore, the administration of air into a patient's body should generally be avoided for medical reasons. Another negative effect of air present in the fluidic system of an infusion pump device is the reduced stiffness of the fluidic system. Due to the high compressibility of gases, such as air in relation to liquids, it becomes difficult to detect blockages or occlusions in the fluidic system of an infusion pump device by measuring the fluidic pressure, because the air reduces the pressure increase that occurs in case of an occlusion.

Filling a container with a liquid medicament with prior removal of air from the container and without air bubbles getting into the container requires skill The user is generally an untrained person, such as the patient himself or a relative. Reservoir containers can be filled by transferring the liquid medicament with a syringe. Syringes are typically inexpensive, but certain manual skills are needed for their proper use. Many patients with motor difficulties, such as diabetics with neuropathy or the elderly, have problems with safely handling syringes. In addition, accidental needle injuries and transferring the proper amount of medication pose concerns. Another problem is cross-contamination of medications between containers.

Present devices should help a user fill a container for infusion pump systems. Those devices, however, are intended for the use in syringe/ampoule type infusion pump systems and cannot be properly used with flexible containers.

Present devices have an infusion system with a flexible reservoir container arranged in a rigid casing and fluidly connected to a liquid in a supply container under ambient pressure. When a vacuum pump reduces the pressure inside of the rigid casing, the resulting pressure differential between the rigid casing and the supply container conveys the liquid into the flexible container. To avoid air, instead of liquid, being emptied into the flexible container from the supply container, the user has to correctly orient the supply container. Because a user usually does not have medical training, such a system is prone to incorrect operation and handling errors. Furthermore, present devices do not allow evacuation of the flexible container prior to filling.

SUMMARY

In one embodiment, a device for transferring a liquid medicament from a supply container to a flexible reservoir container is disclosed. The device may comprise a compartment unit and an adapter unit. The compartment unit may comprise a sealingly closable evacuation chamber, arranged for housing the flexible reservoir container and for being fluidly connected with a pump mechanism. The adapter unit may comprise at least one transfer passage for transferring liquid from a supply container connected to the adapter unit to the flexible reservoir container. A separator may be arranged in the transfer passage for separating gas bubbles from a liquid streaming through the transfer passage, the separator being fluidly connected to the chamber.

In another embodiment, a kit comprising a device, according to any of the embodiments disclosed herein, and one or more flexible reservoir containers.

In still another embodiment, a method for transferring a liquid medicament from a supply container to a flexible reservoir container is disclosed. The method may comprise one or more of the following acts: providing a fluid connection between the supply container and the flexible reservoir container; providing a separator arranged in the fluid connection for separating gas bubbles from the liquid; subjecting the flexible reservoir container to a reduced ambient pressure, thereby generating a negative pressure inside of the flexible reservoir container; sustaining normal ambient pressure inside of the supply container; subjecting the separator to the reduced ambient pressure, wherein the separation of the gas bubbles from the liquid in the separator is effected by the pressure difference between the liquid and the reduced ambient pressure; and conveying the liquid from the supply container to the flexible reservoir container, driven by the pressure difference between the inside of the supply container and the inside of the flexible reservoir container.

These and other features and advantages of these and other various embodiments of the present invention will become more apparent in view of the drawings, detailed description, and claims provided that follow hereafter.

BRIEF DESCRIPTION OF THE DRAWINGS

The following detailed description of the embodiments of the present disclosure can be best understood when read in conjunction with the following drawings, where like structure is indicated with like reference numerals, and in which:

FIGS. 3A, 3B and 3C schematically show other embodiments of a device according to one or more embodiments with a detachable adapter unit;

FIG. 4 shows a possible embodiment of a pressure controlled valve for use in a device according to FIG. 3C;

FIGS. 8A and 8B show the adapter unit of FIG. 7, in a closed state (FIG. 8A), and in an open state (FIG. 8B);

FIGS. 12A-12E show an alternative embodiment of a device.

Figure 1:
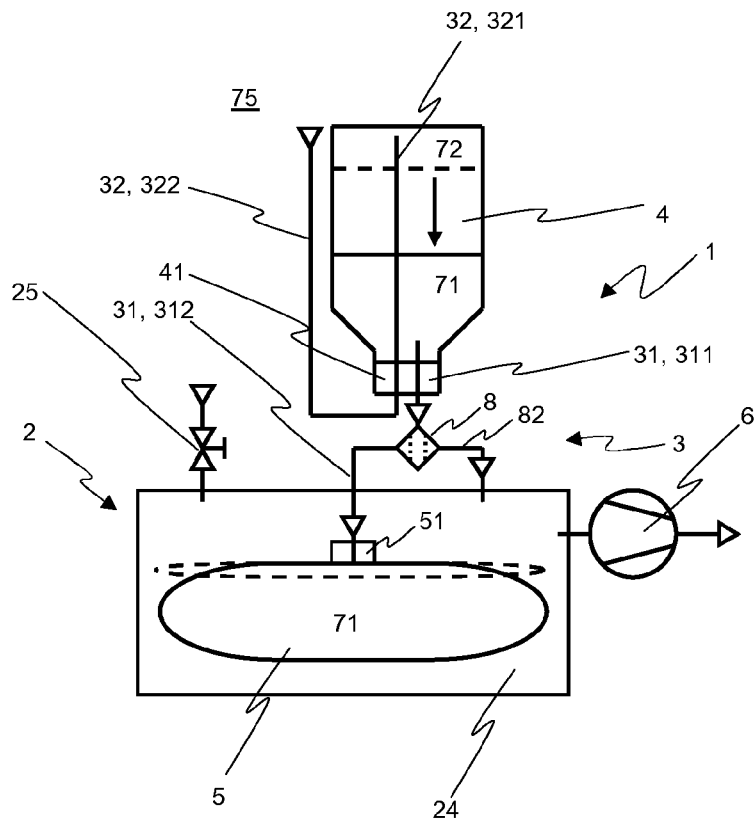
FIG. 1 schematically illustrates a device according to one or more embodiments for transferring a liquid medicament from a supply container to a flexible reservoir container.

Skilled artisans appreciate that elements in the figures are illustrated for simplicity and clarity and have not necessarily been drawn to scale. For example, the dimensions of some of the elements in the figures may be exaggerated relative to other elements, as well as conventional parts removed, to help to improve understanding of the various embodiments of the present disclosure.

DETAILED DESCRIPTION

The embodiments described herein are not intended to be exhaustive or limit the disclosure to specific forms disclosed. Instead, the embodiments selected for description have been chosen to enable one skilled in the art to practice the disclosure.

In one embodiment, a device for transferring a liquid medicament from a supply container to a flexible reservoir container has a compartment unit and an adapter unit is disclosed. The compartment unit may comprise a sealingly closable evacuation chamber, arranged for housing the flexible reservoir container and for being fluidly connected with a pump mechanism. The adapter unit may comprise at least one transfer passage for transferring liquid from a supply container connected to the adapter unit to the flexible reservoir container. A separator may be arranged in the transfer passage for separating gas bubbles from a liquid streaming through the transfer passage.

In another embodiment, the separation of the gas bubbles from the liquid stream in the separator is affected by a negative pressure in the chamber of the compartment unit. The separator can be fluidly connected to the chamber, and may comprise a liquid-impermeable, gas-permeable membrane that is on one side fluidly connected to at least one transfer passage and on the other side, fluidly connected to the chamber. The separator may comprise a liquid-permeable, hydrophilic membrane or filter arranged in at least one transfer passage.

Another embodiment of the device according to the disclosure may comprise at least one vent passage for venting ambient air into the supply container.

In another embodiment, the device may comprise a main valve and/or a flow restrictor arranged in the transfer passage upstream of the separator. Optionally, the main valve can be controlled by the pressure in the chamber.

According to another embodiment, the adapter unit of a device may be detachable and can be detachably secured and sealingly connected to the compartment unit.

In another embodiment, the compartment unit may comprise two casing parts that can be detachably secured to each other, thereby forming the sealingly closed chamber. The adapter unit can be detachably secured to one of the casing parts of the compartment unit. One of the casing parts may provide a fluid connection of a flexible reservoir container arranged in the chamber with the transfer passage of the adapter unit.

In still other embodiments, the device can be equipped with a pump port or connector for fluidly connecting the chamber with a pump mechanism. The device also may comprise a pump mechanism. In another embodiment, a flexible reservoir container can be mounted in the chamber.

In another embodiment, a kit may be provided which comprises a device according to the present disclosure and one or more flexible reservoir containers. In another embodiment, the kit may comprise one or more casing parts, in which a flexible reservoir container can be mounted. In another embodiment, the one or more flexible reservoir containers may be mounted in the casing parts. The kit may comprise one or more syringes as a pump device.

In a further embodiment, a method for transferring a liquid medicament from a supply container to a flexible reservoir container is disclosed. The method may comprise one or more of the following acts: providing a fluid connection between the supply container and the flexible reservoir container; providing a separator arranged in the fluid connection for separating gas bubbles from the liquid; subjecting the flexible reservoir container to a reduced ambient pressure, thereby generating a negative pressure inside of the flexible reservoir container; sustaining normal ambient pressure inside of the supply container; subjecting the separator to the reduced ambient pressure, wherein the separation of the gas bubbles from the liquid in the separator is affected by the pressure difference between the liquid and the reduced ambient pressure; and conveying the liquid from the supply container to the flexible reservoir container, driven by the pressure difference between the inside of the supply container and the inside of the flexible reservoir container.

In a still further embodiment, the method may include evacuating air via the separator, prior to filling the flexible reservoir container. The separator is designed in such a way that the flexible reservoir container is fluidly connected to its surroundings with its reduced ambient pressure as long as the separator has not yet come into contact with liquid. Reference is now made to the various illustrated embodiment depicted by the figures.

A basic embodiment of a device 1 for transferring a liquid from a supply container 4 to a flexible reservoir container 5, is schematically shown in FIG. 1. The supply container 4, here a vial containing a liquid medicament, such as insulin solution, is connected to an adapter unit 3 of the device 1, comprising a vent passage 32 and a transfer passage 31.

In the shown embodiment, the vent passage 32 comprises a first hollow needle 321 for penetrating a septum 41 of the supply container 4. The length of the first needle 321 is chosen so that in a bottom-orientation of the vial 4 the opening of the first needle is as high as possible to reduce the generation of air bubbles when ambient air 72 is vented into the container 4 during the liquid transfer process. In one embodiment, the tip of the first needle 321 is located above the liquid 71 phase when the vial is not yet completely filled. The first needle 321 is in fluid communication with a vent conduit 322 of the vent passage 32, opening toward ambient atmosphere 75. To avoid any possible contamination of the vial content, a filter, such as a gas permeable membrane, can be provided at the entry of the vent passage 32.

The transfer passage 31 comprises a second hollow needle 311 for penetrating the septum 41 of the container 4. The second needle is considerably shorter than the first needle 321, in order to ensure that in the applied bottom-up orientation the vial can be completely emptied. Furthermore, a large distance between the openings of the first and second needle avoids the inadvertent transfer of vented air into the liquid transfer passage.

A compartment unit 2 of the device 1 comprises a sealingly closed evacuation chamber 24, in which the flexible container 5 to be filled can be arranged and mounted. The initially empty flexible reservoir container 5 (dashed line) is connected with a transfer conduit 312 of the transfer passage 31, via a port 51 of the flexible reservoir container or the container 5 itself.

As depicted in FIG. 1, in some embodiments, the flexible containers may comprise the port 51 internally as an internal port. However, any suitable type of flexible container may be used. It is also possible to use flexible containers without an internal port that can be connected to an external connector that acts as an external port. For example, in one embodiment, the external port may be embodied as an integral part of the compartment unit of the device. For example, and not limited thereto, suitable flexible containers for use in device 1 are disclosed in European patent application No. 08167548.0, as well as suitable external connectors are disclosed in European patent applications No. 08170627.7 and 09155279.4, which are hereby incorporated by reference in their entirety.

To avoid the previous problems noted above in the background, the transfer passage 31 does not provide a direct connection between the supply container 4 and the flexible reservoir container 5. To prevent the transfer of air bubbles or larger amounts of air into the flexible reservoir container 5, a gas-liquid separator 8 is arranged in the transfer passage 31 for separating gas bubbles from the stream of transferred liquid and, if needed, to branch off gas streaming through the transfer passage. In one embodiment, such a separator 8 comprises a gas-permeable membrane that is arranged in fluid connection to the transfer passage 31. The drain of the gas bubbles through the membrane is driven by a pressure differential across the membrane between the transfer passage 31 and the other side of the membrane, which for that purpose is in fluid connection 82 with the evacuation chamber 24. The chamber 24 provides a negative pressure during the transfer process. The transfer passage can also comprise a bubble trap in order to retain air bubbles in the liquid stream and to give the bubbles enough time to pass through the gas permeable membrane.

Another possibility is the use of a gas-liquid separator 8, where a gas-permeable membrane is arranged adjacent to a liquid-permeable membrane to allow the separation of liquid and gas. The gas-permeable membrane and the smaller liquid-permeable membrane are arranged in parallel, with a small gap separating them. The width of the gap is chosen in a way that, for energetic reasons, air bubbles are prevented from entering the gap and covering the liquid-permeable membrane, where the mere suction force could urge the air bubble through the liquid-permeable membrane.

Referring to FIG. 1, during normal use of the device 1, the flexible reservoir container 5 is mounted in the evacuation chamber 24 of the compartment unit 2 and fluidly connected to the transfer conduit 312 of the transfer passage 31. Then, a supply container 4, such as a vial with liquid medicament, is connected with the adapter unit 3 by penetrating the septum 41 of the vial with the first 321 and second 311 hollow needle. In an exemplary embodiment, the adapter unit 3 is designed in such a way that the needles 321, 311 automatically penetrate the septum 41 when the supply container 4 is secured to the adapter unit 3, for example, during insertion of the vial into a corresponding receptacle 34.

If it has not previously occurred, the evacuation chamber 24 is now sealingly closed and the chamber venting valve 25 is closed. Then the pump mechanism 6 is actuated, reducing the pressure inside of the evacuation chamber 24. The negative pressure can, for example, lie between about −250 mbar to about −850 mbar in one embodiment, and between about −650 mbar and about −750 mbar in another embodiment. The exact values depend on the particular embodiment of the device and the container to be filled, and may lie above or below the before-mentioned values.

In another embodiment, the pump mechanism 6 can be, for example, a manually operated piston pump, or even a syringe fluidly connected to the evacuation chamber 24. In an alternative embodiment, the pump mechanism may be a motor-driven pump. As a result of the negative pressure inside of the evacuation chamber 24, the higher ambient pressure in the vial propels the liquid 71 via the transfer passage 31 into the flexible container 5, while ambient air is constantly vented into the vial via the vent passage 32. The liquid stream 74 enters the second needle 311, passes the separator 8, where any air bubbles 73 carried along the stream 74 are diverted through the gas-permeable membrane 81 and degassing conduit 82 to the evacuation chamber 24, and flows into the flexible reservoir container 5. During filling, the flexible container 5 is inflated (black line).

To finish the transfer process, either the transfer passage is blocked, for example by closing a valve arranged in the transfer passage, or the chamber venting valve 25 may be opened, thereby venting the evacuation chamber 24 and reducing the pressure differential to zero. The filled flexible reservoir container 5 is then ready for use in an infusion pump system.

When the flexible reservoir container is filled, its walls are under a certain strain, which leads to certain over pressure in the flexible reservoir container. To prevent the flow of liquid out of the filled flexible reservoir container 5 though the transfer passage 31 when the negative pressure in the chamber 24 is removed, a check valve (not shown) may be arranged in the transfer passage 31, upstream of the separator 8.

In some embodiments, a mechanism is provided to inform a user when the negative pressure has reached a certain value, particularly when the pump mechanism is actuated manually. Such a mechanism may, for example, give the user a visual or acoustical signal.

Figure 2:
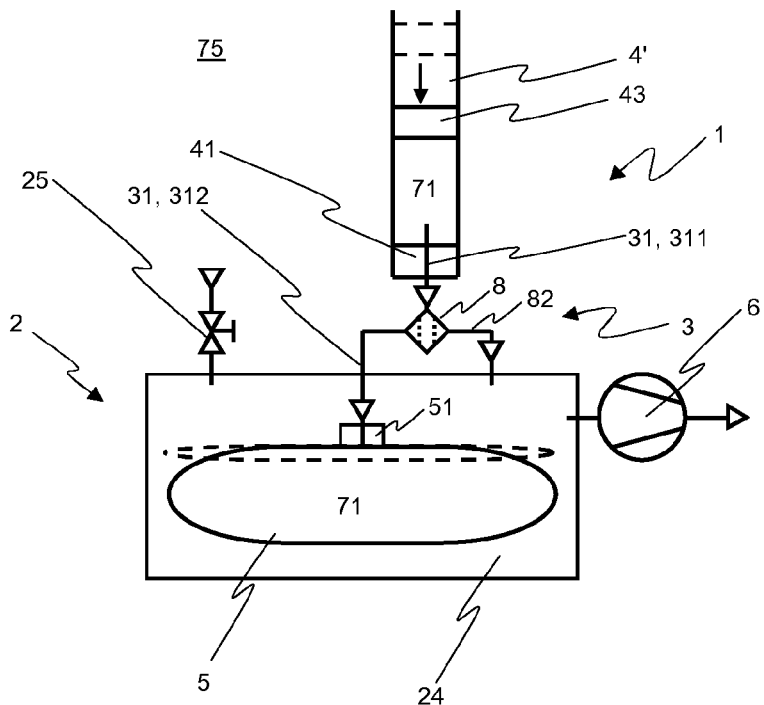
FIG. 2 schematically illustrates an alternative device according to one or more embodiments for transferring a liquid medicament from a supply container to a flexible reservoir container.

An alternative device is shown in FIG. 2, suitable to work with an ampoule 4' with movable plug 43. Such ampoules are intended for the use with injection pen systems, particularly for insulin injection pens, and comprise a certain volume (e.g. 3 ml) of liquid medicament between a septum and a movable plug. Ambient pressure in the ampoule 4' is automatically sustained, since the movable plug 43 constantly reduces the volume of the ampoule during the draining of the ampoule. As a result, the venting passage 32 used in the embodiment of the device of FIG. 1 is not necessary.

This embodiment of a device is suitable for some manufacturers of liquid medicaments, particularly of insulin solutions, because they directly provide their products in such prefilled injection pen cartridges. Thus, a user of a device can fill a flexible reservoir container with any medicament, without restriction.

Figure 3A:
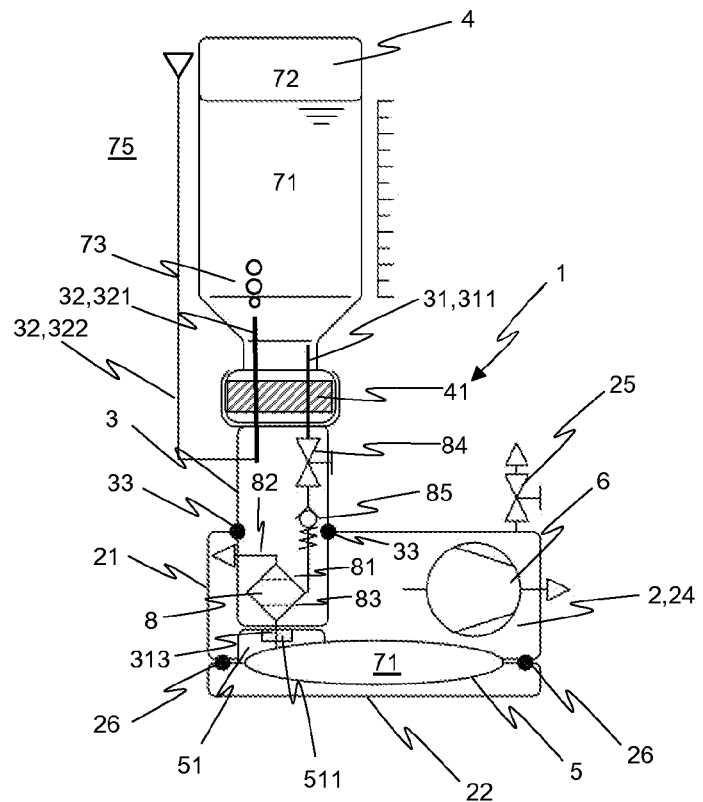

Another embodiment of a device is illustrated in FIG. 3A. The compartment unit 2 comprises two casing parts 21, 22 that are sealingly connected to form the evacuation chamber 24. In order to mount the flexible reservoir container 5, one of the casing parts 21, 22 can be detached from the compartment unit 2. Once the flexible reservoir container is mounted, the casing parts are reassembled.

In another embodiment, the adapter unit 3 is a detachable unit that can be secured to the compartment unit 2 of the device, thereby establishing the fluid connections between the port 51 of the flexible reservoir container, the separator 8 and transfer passage 31 of the adapter unit 3, and the evacuation chamber 24. A third hollow needle 313 is provided at the end of the transfer passage 31, which can penetrate a septum 511 arranged in the port 51 of the flexible reservoir container 5.

The first hollow needle or pin 321 is longer than the second hollow needle 311, but does not reach the air phase 72. The distance of the tips of the needles 321, 311 is sufficient to prevent any air moving from the vent passage 32 into the transfer passage, and gas bubbles 73 flowing in through the first needle 321 ascend to the air phase 72. The entry into the venting conduit 322 is located above the maximum possible filling level of the vial 4. Thus, no liquid 71 can emerge through the vent passage 32 even if no pressure is applied to the transfer passage 31.

The adapter unit 3 is designed such that when mounted to the compartment unit 2 a sealing 33 provided on the adapter unit 3 and/or the compartment unit 2 sealingly closes the evacuation chamber 24.

A liquid-permeable membrane or filter of a separator 8 for use with aqueous solutions, in which liquid medicaments are normally provided, comprises a hydrophilic material that, when wetted, effectively prevents the passage or air bubbles due to interface tension. As long as such a liquid-permeable membrane or filter is dry, however, it remains permeable for air. In this embodiment, an evacuation step can precede the liquid transfer step. Since the liquid-permeable membrane is not yet wetted and still gas-permeable, the flexible reservoir container 5 is in fluid communication with the evacuation chamber 24, via a temporary evacuation passage comprising third needle 313, transfer conduit 312, separator 8, and degassing conduit 82.

When evacuation chamber 24 is evacuated with the pump mechanism 6, a main valve 84 upstream of the separator 8 remains closed, and the inner volume of the flexible reservoir container 5 is evacuated via the temporary evacuation passage. Since there is a certain pressure drop over the two membranes of the separator 8, the pressure in the evacuation chamber 24 should be reduced slowly, in order to remain in a static regime where the pressure drop is irrelevant. Alternatively or additionally to slow evacuation, the pressure inside the evacuation chamber 24 may be increased again and the evacuation step repeated. When the flexible reservoir container 5 is completely evacuated, the main valve 84 is opened. The liquid flows now from the supply container 4 through the transfer passage 31 to the flexible reservoir container 5. When the liquid passes the separator 8 the liquid-permeable membrane 83 is wetted and becomes gas-impermeable. The temporary evacuation passage is now closed and the primary function of the separator 8 is established.

In the embodiment shown in FIG. 3A, a main valve 84 is provided upstream of the separator 8, which allows the closing of the transfer passage 31. This embodiment not only allows the stop of fluid transfer by closing the main valve, it also allows to delay the transfer of the liquid 71 in the supply container 4 to the flexible reservoir container 5. This feature eventually allows the evacuation of the flexible reservoir container 5 prior to the filling process, in order to reduce the amount of remaining air in the flexible reservoir container 5.

In addition to the main valve 84, a check valve 85 is provided, preventing any air or liquid in the transfer passage from flowing backwards. The two valves 84, 85 provide some redundancy. The check valve 85 ensures that even when a manipulation error with main valve 84 occurs, no liquid can flow back from the flexible reservoir container 5. The device would also work without the main valve 84 and only the check valve 85, although in such a case it would not be possible to evacuate the flexible reservoir container prior to the filling step.

Once the separator 8 is wetted, the temporary evacuation passage is irreversibly closed, the above-mentioned embodiment is particularly advantageous in combination with a disposable adapter unit, in which after each filling procedure the detachable adapter unit, containing all potentially contaminated parts, is replaced.

Figure 3B:
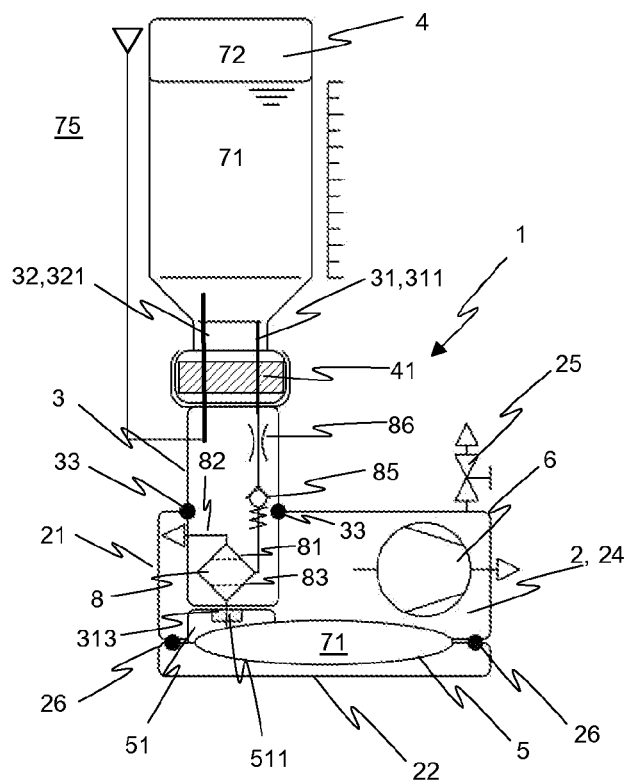

An alternative embodiment of a device 1 is shown in FIG. 3B. Instead of a main valve, this embodiment comprises a flow restrictor 86. Such a flow restrictor can be realized as a meandering channel with a diameter of 50 to 250 micrometers, or a capillary. This allows an antecedent evacuation act without the need of an additional act of the user, e.g., the actuation of the main valve 85 of the embodiment in FIG. 3A. After the evacuation chamber 24 has been evacuated with the pump mechanism 6, the liquid starts to flow from the supply container 4 into the transfer passage 31. In the flow restrictor 86, the liquid stream is delayed for a certain time, which allows the remaining air in the flexible reservoir container 5 to be sucked into the evacuation chamber 24 before the liquid stream reaches the separator 8 and closes the temporary evacuation passage.

Another embodiment of a device 1 is shown in FIG. 3C. In that particular embodiment, the user actuated main valve 84 of FIG. 3A is replaced by a pressure controlled main valve 84', which is controlled by the pressure differential between the ambient atmosphere 75 and the evacuation chamber 24. When the flexible reservoir container 5 is sufficiently evacuated the negative pressure reaches a certain value, for example −750 mbar. The main valve 84' opens automatically and the transfer process starts. Such an embodiment reduces the user's acts to a minimum while reproducibly controlling the evacuation and filling of the flexible reservoir container.

In an alternative embodiment, the check valve 85 can be skipped. Since venting of the evacuation chamber 24 leads to a pressure drop, the pressure controlled valve 84' will automatically close, preventing the liquid from flowing backwards. Even if the supply container 4 is removed from the adapter unit 3 prior to venting the evacuation chamber 24, which does not immediately cause the valve 84' to close, ambient air will be sucked into the evacuation chamber 24 via the needle 311, separator 8 and degassing conduit 82, preventing any liquid from flowing backwards and slowly venting the evacuation chamber 24. This causes the main valve 84' to close.

A possible embodiment of a pressure regulated valve 84' that can be used in the device referred to in FIG. 3C is shown in FIG. 4. The valve 84' comprises a valve seat 843 arranged in a conduit of the transfer passage 31 and a valve member 842 in the form of a resilient elastic membrane arranged above the valve seat 843 and sealingly closing the conduit. The other side of the membrane 842 is in fluid communication 82 with the evacuation chamber 24 and, thus, subject to the pressure in the evacuation chamber. The resilient flexible membrane 842 is chosen such that when the pressure differential between the transfer passage 31 and the evacuation chamber 24 is below a certain value, the membrane 842 bulges and the liquid stream 74 can pass the valve 84'.

Figure 5:
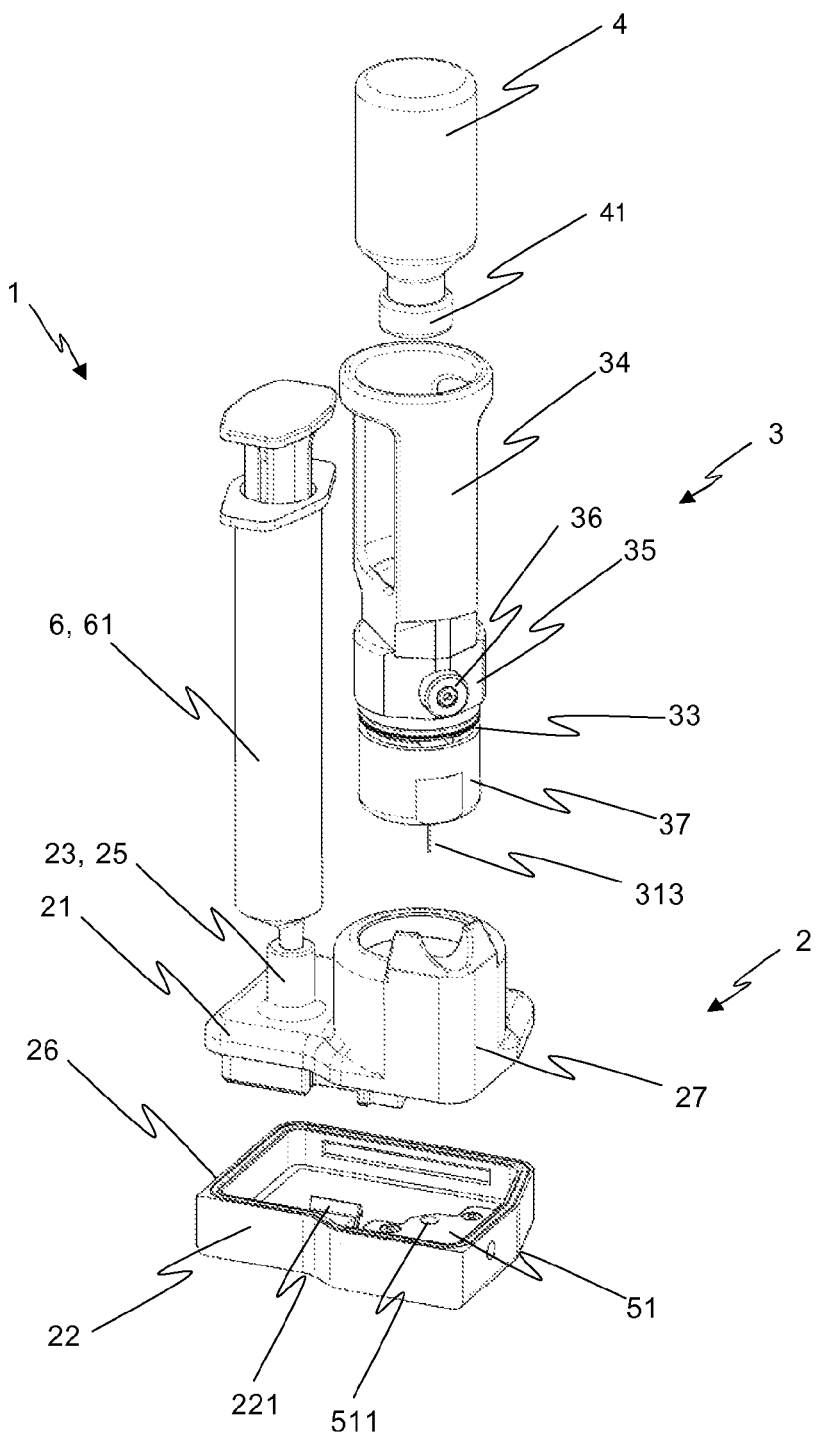
FIG. 5 shows a possible embodiment of a device in an exploded view.

Another embodiment of a device 1 is shown in an exploded view in FIG. 5. The device comprises a compartment unit 2 with a first 21 and a second 22 casing part, and an adapter unit 3.

The adapter unit 3 has an adapter casing 35 and a supply container receptacle 34, the latter being designed to accommodate and secure a supply container 4 in the form of a vial, e.g. a standard insulin vial of 10 ml volume.

A supply container 4 can be engaged to the adapter unit 3 with the neck 42 of the supply container 4 facing downwards. The neck is inserted into the supply container receptacle 34 in a generally linear fashion. The supply container 4 is centered and guided in the first part of the engagement movement. During engagement, the first and second hollow needle (not visible) pierce the septum 41 of the supply container 4, thereby creating flow paths to the inside of the supply container 4. In addition, the supply container receptacle 34 may be provided with catches that engage with the neck of the supply container in the final part of the engagement movement.

The casing 35 is essentially cylindrical in shape. The section oriented toward the compartment unit 2 forms a connector part 37, to be connected with a corresponding connector part 27 of the compartment unit 2. A circumferential sealing 33 provides an air tight connection between the adapter unit 3 and the compartment unit 2 when attached together. The sealing may be realized as an O-ring or by two-component injection molding, the sealing being made by a soft component.

A first casing part 21 of the compartment unit 2 comprises a connector part 27 intended to interact with the adapter unit 3, in the form of an open cylinder into which the adapter connector part 37 can be inserted. A pump port 23 is provided for connecting the evacuation chamber 24 of the compartment unit 2 with an external pump mechanism 6, here embodied as a standard syringe 61. Syringes are inexpensive and, thus, provide a suitable manually operated pump. There is no risk of injury, because no needle is needed.

In interaction with the syringe 61, the pump port 23 can act as a venting valve 25, because when the syringe in inserted into the port, the chamber 24 is closed (venting valve 25 closed) and when the syringe is removed from the port, the chamber 24 communicates with the ambient atmosphere (venting valve 25 open).

A second casing part 22 comprises a circumferential sealing 26. It also comprises a port 51 for connecting a flexible reservoir container (not shown) with the hollow pin 313 of the adapter unit 3. Simultaneously, the port 51 is designed to secure the flexible reservoir container to the second casing part 22.

Referring to FIG. 5, an embodiment of a device 1 is shown. For hygienic reasons, all parts of the device that come into contact with the liquid medicament are replaced after a single filling procedure. Since all these parts are located in the adapter unit 3, it is sufficient to design the adapter unit 3 as a disposable part, while the compartment unit 2 can be reused several times. This is advantageous if the pump mechanism used is not a standard syringe, but is somewhat more complicated or more expensive.

In the shown embodiment, the second casing part 22 allows mounting of the flexible reservoir container 5 and fluidly connecting it to 51 with the adapter unit 3. The port 51 would have to be replaced together with the used disposable flexible reservoir container. However, the filled flexible reservoir container 5 can be transferred to its destination in an infusion pump device while still mounted on the second casing part 22, because the rigid structure of the casing 22 protects the flexible reservoir container and simplifies the handling for the user. In the infusion pump device, the second casing part 22 also acts as a part of the casing of the infusion pump device. After use, the casing part 22 and the emptied flexible reservoir container are disposed.

FIG. 6 depicts a cross-sectional view of a compartment unit 2 of a device 1, similar to FIG. 5, with (a) a first casing part 21 and (b) a second casing part 22. In order to limit the expansion of a flexible reservoir container 5 during the filling process, thereby defining a maximum filling volume and also preventing an accidental damage of the flexible reservoir container due to overfilling, the first 21 and second 22 casing parts each comprise a support structure 28, 28'.

In the first casing part 21, the support structure 28 is a curved wall with a plurality of venting conduits 281 in the form of holes. The wall 28 divides the evacuation chamber 24 formed by the two casing parts into two halves, an upper half above the wall 28, toward which the pump port 23 and the connector 27 are opening, and a lower half below the wall 28, where the flexible reservoir container 5 is arranged. The surface of the wall facing the lower part of the evacuation chamber is concavely shaped. When the evacuation chamber is evacuated, the air in the lower half is evacuated through the holes 281 into the upper half and then to the pump mechanism 6. The volume of the upper half provides the negative pressure reservoir when the flexible reservoir container 5 is filled. Finally, the volume of the lower half of the evacuation chamber decreases toward zero.

A similar hollow support structure 28' is provided in the second casing part 22, where the bottom of the casing wall is concave. In order to allow the complete expansion of the flexible reservoir container 5 toward the support structure 28', a network of open channels 281' is provided on the support structure 28', which allows the communication of the negative pressure to the lower flexible reservoir container during all states of expansion.

Figure 6A:
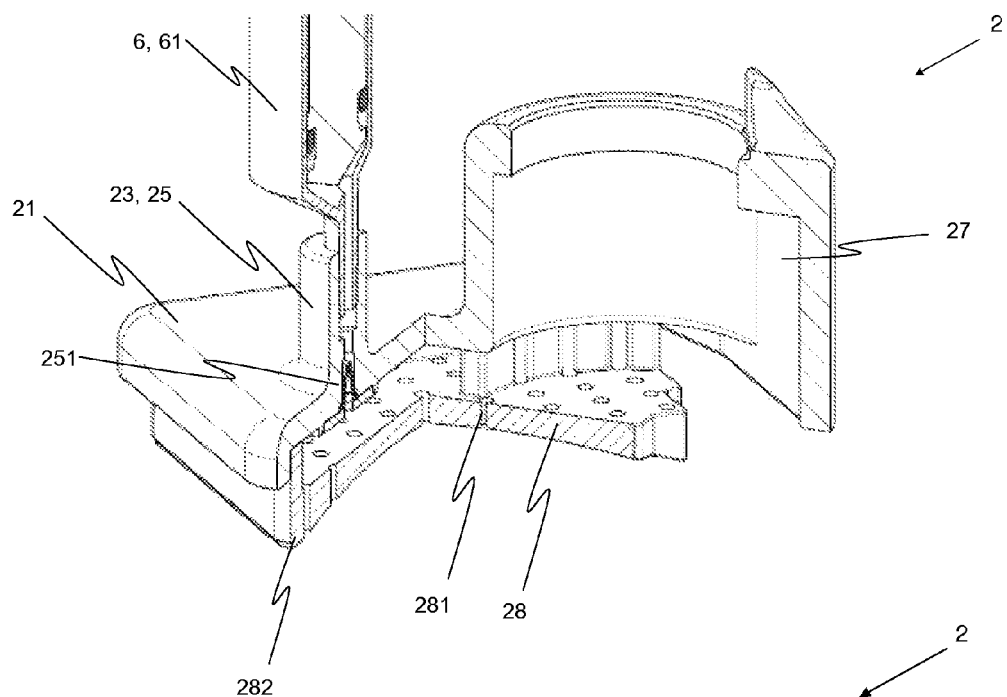
FIGS. 6A and 6B show the casing part of a device similar to FIG. 5, providing a hollow support structure limiting the expansion of a flexible reservoir container.
Figure 6B:
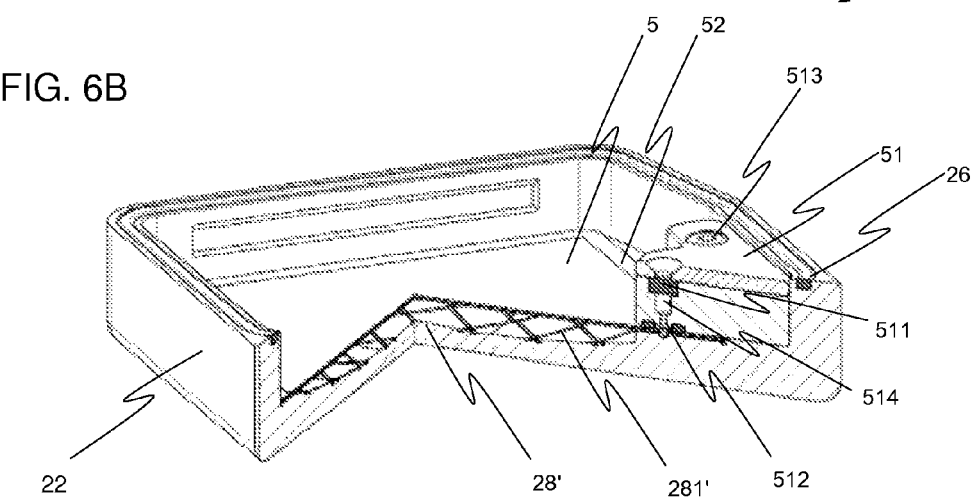

In FIG. 6B, the completely empty flexible reservoir container 5 is shown mounted to the second casing part 22. The flexible reservoir container 5 is clamped between the wall of the casing part 22 and an external port element 51. The port element 51 is not an integral part of the flexible reservoir container 5 itself. Two screws 513, one of which is visible, secure the port element 51 to the casing part 22, thereby clamping a corner of the flexible reservoir container 5. The container is provided with holes in a peripheral sealing area (not visible) to prevent the screws from damaging the container hull.

The port element 51 comprises a conduit 514 for fluidly connecting the transfer passage 31 of the adapter unit 3 with the flexible reservoir container. A septum 511 arranged in the conduit can be penetrated by a hollow needle or pin 313 of the transfer passage 31, thereby establishing a fluid connection. A circumferential sealing 512 provides a liquid-tight connection between the conduit 514 and an opening of the flexible reservoir container.

The shown flexible reservoir container 5 is designed with a preformed fluid channel. The container also shows a clamp and connection system similar to the one formed by the casing part 22 and the port element 51.

When mounted to the second casing part 22, the outer rim 52 of the flexible reservoir container 5 lies on a circumferential edge of the bottom wall 28' of the casing part 22. The first casing part 21 is provided with a similar edge 282. When the two casing parts are assembled, the rim 52 of the flexible reservoir container is optionally secured between the edges of the support structures 28, 28'.

The first casing part 21 is provided with a pump port 23 in fluid connection with the upper part of the evacuation chamber 24. The pump port comprises a check valve 251 to avoid venting of the evacuation chamber when the syringe 61 connected to the port 23 is removed.

In addition, a second check valve may be provided that allows the exhaust of the air in the syringe 61 to the ambient atmosphere when the piston of the pump mechanism is pushed. This would allow a user to perform several pumping strokes to evacuate the evacuation chamber 24, using a syringe with a smaller stroke volume.

In an alternative embodiment to the one shown in FIG. 6, the support structure 28 may also be realized as a part of the second casing part 22. This has the advantage that when the first casing part is removed, the filled flexible reservoir container 5 is protected against accidental mechanical damages.

Figure 7:
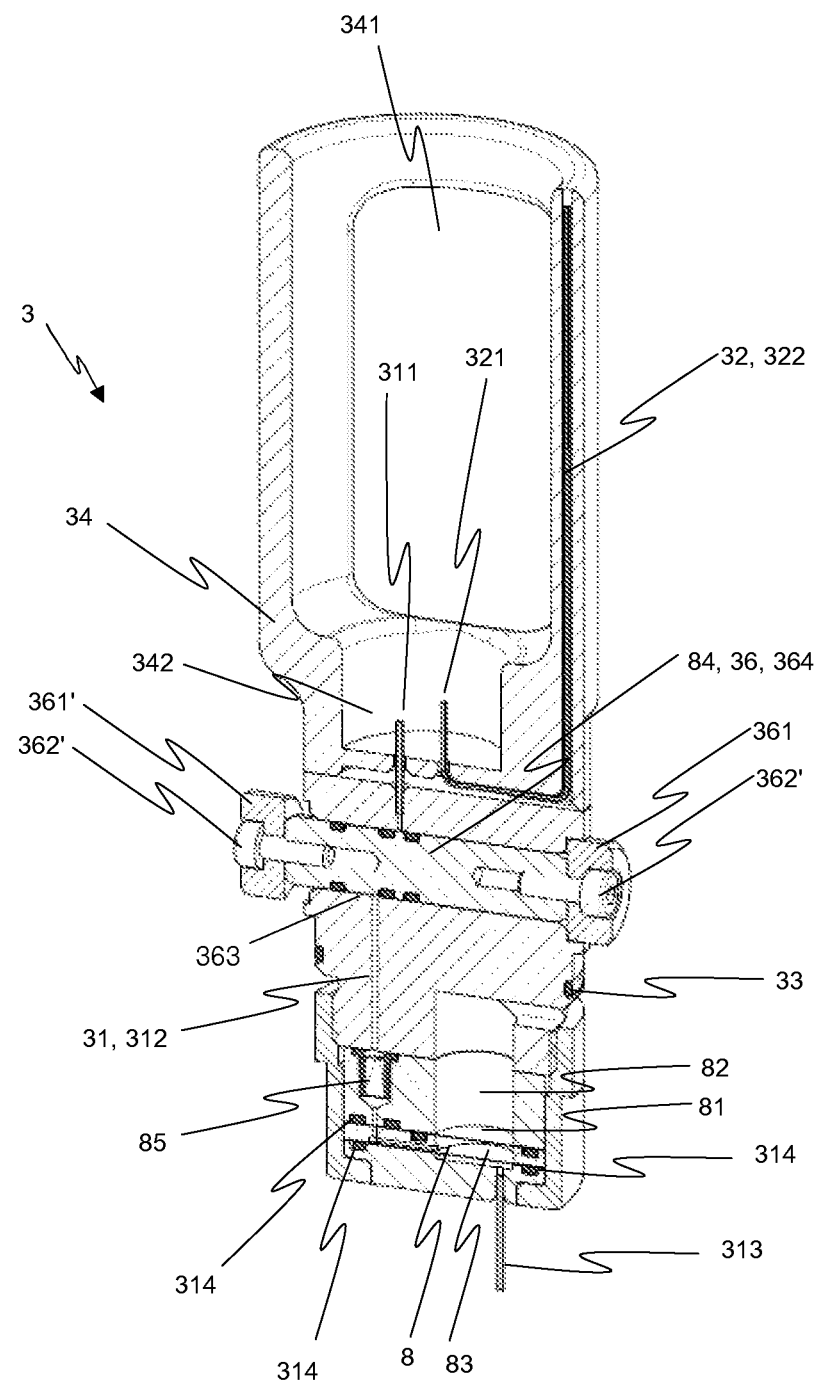
FIG. 7 shows a cross-sectional view of an embodiment of an adapter unit of a device.

An exemplary embodiment of an adapter unit 3 of a device is shown in a cross-section in FIG. 7. The supply container receptacle 34 has two access openings or windows 341 that allow a user to see the label of the inserted supply container. In addition, the windows 341 allow the user to easily grasp an inserted supply container and to remove it from the adapter unit 3.

The hollow needles or pins 311, 321 of the vent passage 32 and the transfer passage 31 are arranged in a recess 342, thereby reducing the risk of an accidental injury by a user. The second needle 311 and the complete vent passage 32 are realized as metallic needles embedded in the body of the supply container receptacle 34, which is made of injection molded plastic. The entry into the venting conduit 322 is located higher than the maximum possible liquid level of a supply container 4. Thus, no liquid can flow out of the vent passage 32 even if no pressure is applied to the transfer passage 31.

The main valve 84 is realized as a slide valve mechanism 36 with a cylindrical slider 364 arranged in a bore of the adapter unit body. In FIG. 7, the valve is in a closed state. The needle 311 and the transfer conduit 312 are fluidly disconnected by a circumferential sealing 363 provided by the surface of the slider 364. Two buttons 361, 361' are fastened to the slider 364 with screws 362, 362'. The two buttons act as stoppers for the slider that define the two working states (open and closed) of the main valve 84.

FIGS. 8A and 8B show the adapter unit with a closed main valve 84 and with an open valve 84, respectively. When a user actuates the valve 84 by pushing the slider 364, the needle 311 and the transfer conduit 312 are fluidly connected via a conduit formed by a channel or groove (not visible) provided on the surface of the slider cylinder. The main valve may have a biased spring element that automatically moves the slider back to a closed position when the user releases the valve.

Downstream of the main valve 84 a check valve 85 (FIG. 8A) is arranged in the transfer conduit 312. The transfer conduit then opens toward a separator 8, with a hydrophilic liquid-permeable membrane or filter 83 and a gas-permeable membrane 81, and ends in the third needle 313.

FIG. 7 shows the adapter unit 3 built from a number of nested subunits. Sealing between the different subunits is achieved by circumferential sealings 314. The two membranes 81, 83 are mounted by sandwiching them between three subunits. In another variant, the sealings are achieved by welding the membranes to the adjacent subunits of the casing.

Figure 9:
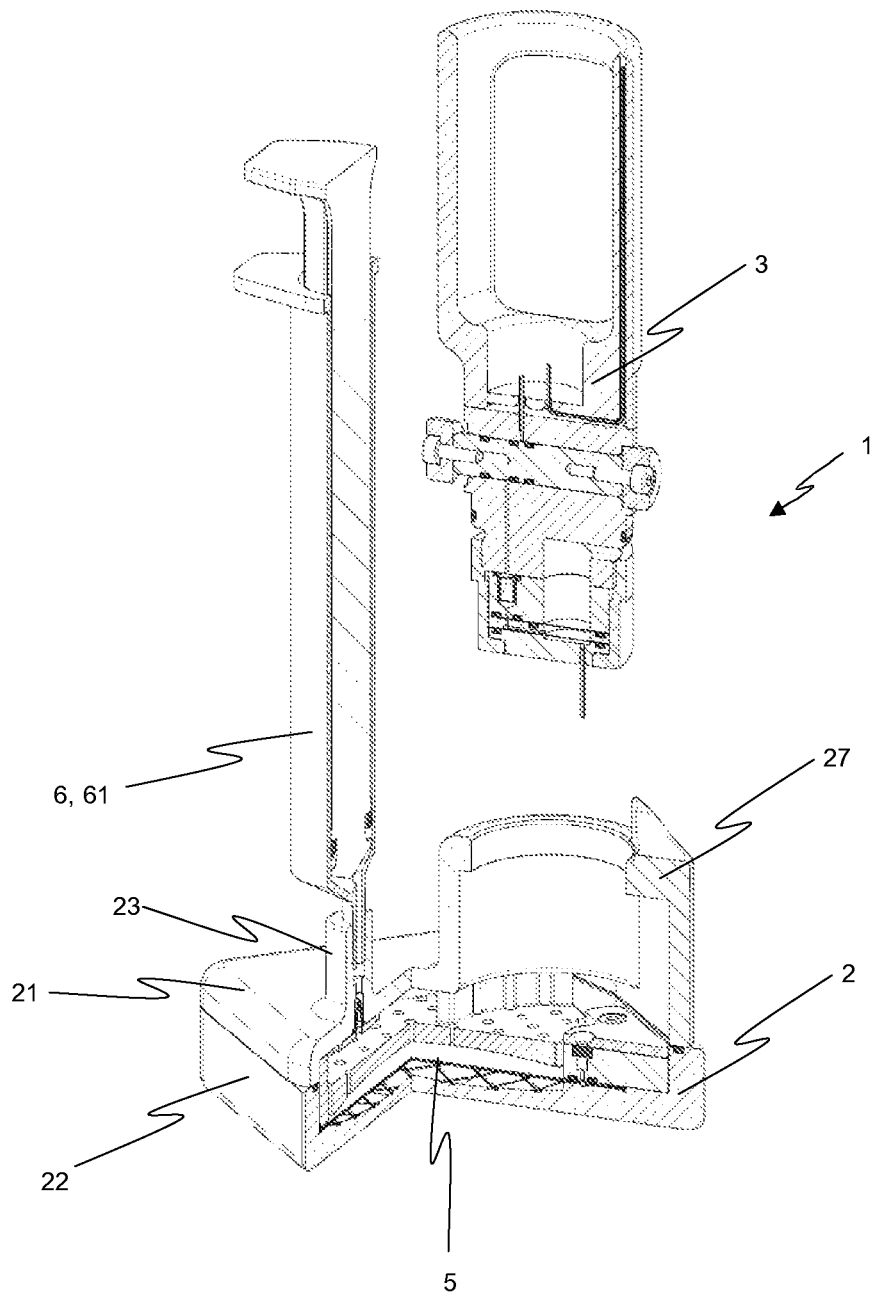
FIG. 9 shows a device with the assembled compartment unit of FIG. 6 together with the adapter unit of FIG. 7.

Another embodiment of device 1 is disclosed in FIG. 9, comprising the assembled compartment unit 2 of FIGS. 6A and 6B together with the adapter unit 3 in FIG. 7. A still empty flexible reservoir container 5 is mounted in the compartment unit 2. A syringe 61 is connected to the pump port 23 and acts as an external pumping mechanism 6.

Figure 10A:
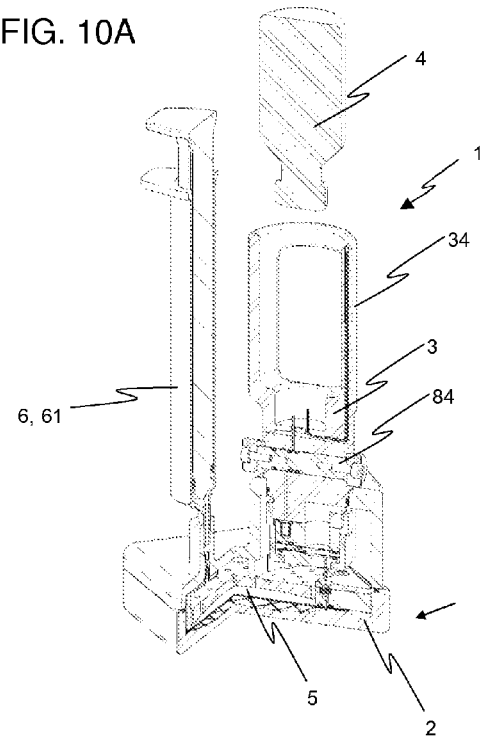
FIGS. 10A-10C show in three consecutive acts the insertion of a vial into the assembled device of FIG. 9 and the evacuation of the chamber.

In the following, the different acts for a proper preparation of the device 1 shall be explained. First, the flexible reservoir container 5 is mounted in the second casing part 22 of the compartment unit 2, as shown in FIG. 6B. Next, the first casing part 21 as shown in FIG. 6A and the second casing part 22 are assembled, arriving at FIG. 9. Then, the adapter unit 3 is inserted into the connector element 27 of the compartment unit 2, arriving at FIG. 10A. The main valve 84 is closed. Then, the vial 4 is inserted into the supply container receptacle 34, arriving at FIG. 10B. Alternatively, the vial 4 may be inserted into the supply container receptacle 34 before the adapter unit 3 is secured to the compartment unit 2. However, such a variant carries the risk that the user may accidentally actuate the main valve 84. Driven by gravity, the content of the vial could then flow along the transfer passage, prematurely wetting the separator, and finally being spilled.

Figure 10C:
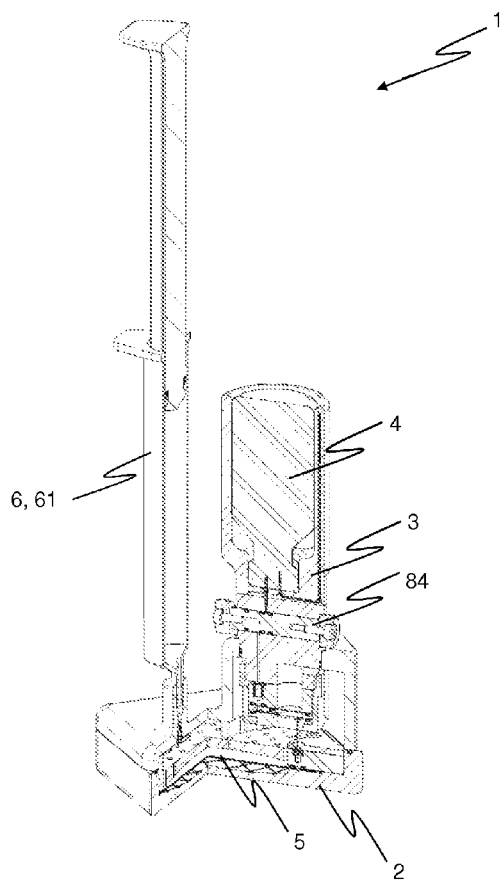
Figure 10B:
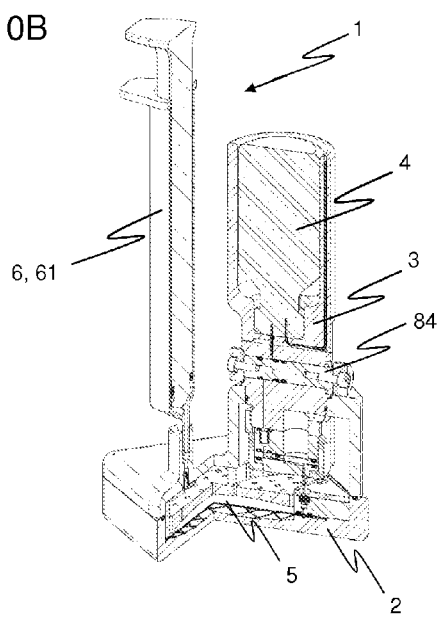

Next, as shown in FIG. 10C, the piston of the syringe 61 is protracted. The main valve 84 remains closed. The pressure in the evacuation chamber 24 of the compartment unit is reduced and any remaining air in the flexible reservoir container 5 is sucked into the evacuation chamber via the dry separator 8.

Finally, the main valve 84 is opened by the user, which causes the liquid in the vial 4 to flow along the transfer passage 31 through the separator 8 into the flexible reservoir container 5. Simultaneously, the vial 4 is vented through the venting passage 32. The flexible reservoir container 5 expands during the filling, and finally its wall sheets reach the support structures 28, 28' of the casing parts. Although there is still a remaining negative pressure, the expansion of the flexible reservoir container 5 is stopped, because its maximum volume is reached.

The user then closes the valve 84, and removes adapter unit 3, thereby venting the evacuation chamber 24. The first, upper casing part 21 is removed. Now, the filled flexible container may be detached from the second casing part 22 and inserted into an infusion pump system. In the shown embodiment, however, the flexible reservoir container does not have an internal port. In this embodiment, the flexible reservoir container 5 remains mounted to the second casing part 22 with its port 51, and is transferred together with the casing part 22 to the infusion pump system, where it is connected to the pump system via the port 51 of the second casing part 22. This approach is useful because the second casing part 22 and port 51 can be reused as a casing part and connector port of the infusion pump system.

In FIG. 11, several embodiments for the design of the venting passage 32 and the transfer passage 31 of the adapter unit in interaction with a liquid filled vial 4 are shown. In FIG. 11A, the tip of the first needle 321 is located in the liquid, while the tip of the venting conduit 322 is located equal to or above the maximum surface level of the liquid in the vial 4. Thus, the liquid 71 cannot flow out of the vent passage 32 for hydrostatic reasons. This embodiment is similar to the one in FIGS. 3 and 9.

Figure 11A:
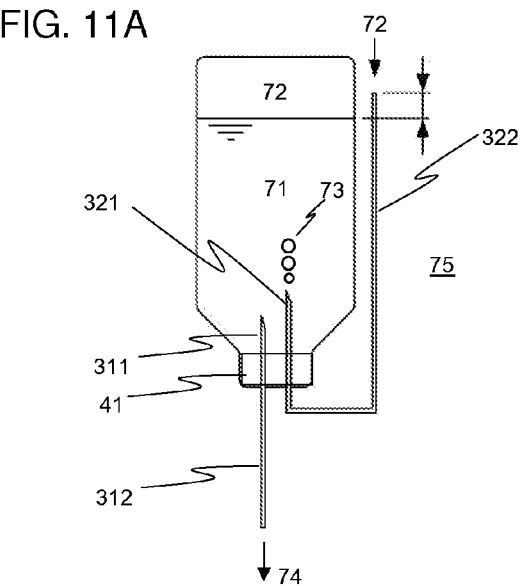
FIGS. 11A-11D show different designs of the venting passage and the transfer passage in interaction with a liquid filled vial.
Figure 11B:
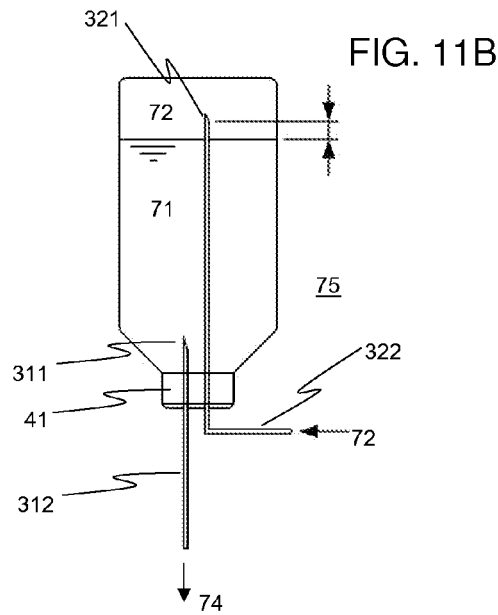

In the embodiment shown in FIG. 11B, the tip of the first needle 321 is above the maximum surface level, similar to FIG. 1. Because no liquid can enter the needle 321, the venting conduit can be shorter, without restrictions to the position of the inlet of the venting conduit 322. This embodiment has the advantage that no air bubbles are produced. The longer needle, however, complicates the handling of it.

Figure 11C:
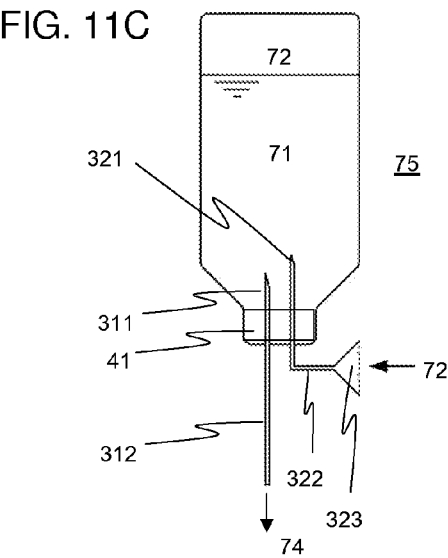
Figure 11D:
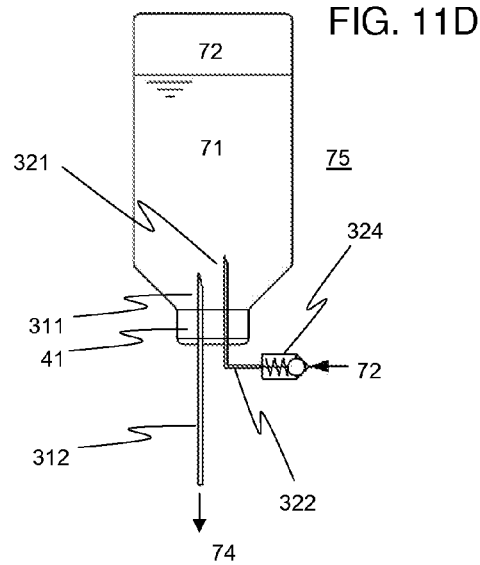

Another embodiment is shown in FIG. 11C. The first needle 321 has its tip located in the liquid 71. To prevent liquid 71 from flowing out of the venting conduit 322, a hydrophobic, gas-permeable membrane 323 is located at the inlet of the venting conduit. While air 72 can enter the inlet through the membrane 323, no liquid can flow out. This approach simplifies the construction of the adapter unit, because the venting passage 32 can be considerably short. A similar embodiment is shown in FIG. 11D, where a check valve 324 is located at the inlet of the of the venting conduit 322.

Another embodiment of a device 1 is shown in FIG. 12. Referring to FIG. 12A, the flexible reservoir container 5 is permanently mounted in a box-like second casing part 22. The flexible reservoir container 5 is equipped with an adapter unit 3 fluidly connected 313 to the flexible reservoir container 5. For simplicity, other aspects, including the needle 321 for the venting passage and the main valve 84, are not shown.

The adapter unit 3 and the empty flexible reservoir container 5 are sterilely packed in the casing part 22, which is covered by a removable cover 29. For example, the casing part 22 may include a peelable protective foil 29. The advantage of such an embodiment is the fact that the second casing part 22, the adapter unit 3 of the device 1 and the flexible reservoir container 5 can include a combined, disposable single-use product.

When a user wishes to fill a fresh flexible reservoir container 5 with a liquid medicament, for example, because the previous flexible reservoir container in his infusion pump system has been emptied, he removes the cover sheet 29 from the casing part/box 22 (FIG. 12B). The user then attaches the durable part of the device 1 according to the disclosure, comprising the first casing part 21 with a manually operated piston pump mechanism 6, as shown in FIG. 12C. A first sealing 26 provided on the first casing part 21 connects the two casing parts 21, 22. A second sealing 33 provided on the first casing part 21 connects the connector parts of the adapter unit 3 and the compartment unit 2. The durable elements 22, 6 of the device 1, which contain the more complex mechanical parts such as the piston pump 6, do not come into contact with the liquid at any time, and, therefore, can be reused.

In another aspect, the supply container/vial 4 with the liquid medicament 71 is inserted top-down into the adapter unit's supply container receptacle 34, and the user manually operates the piston pump 6 (FIG. 12D). The negative pressure in the evacuation chamber 24 conveys the liquid 71 in the vial 4 through the adapter unit 3 into the flexible reservoir container 5.

After completion of the filling, the evacuation chamber 24 is vented, and the durable elements 22, 6 of the device are removed for later use. The contaminated adapter unit 3 is disposed. The filled flexible reservoir container 5, still mounted in the second casing part 22, is then attached to an infusion pump system 9 (FIG. 12E). If the flexible reservoir container 5 is emptied, it is removed from the infusion pump device and disposed, along with the second casing part 22.

For the purposes of describing and defining the present invention, it is noted that the term "about" is utilized herein to represent the inherent degree of uncertainty that may be attributed to any quantitative comparison, value, measurement, or other representation. The terms "about" is also utilized herein to represent the degree by which a quantitative representation may vary from a stated reference without resulting in a change in the basic function of the subject matter at issue.

The above description and drawings are only to be considered illustrative of exemplary embodiments, which achieve the features and advantages of the present invention. Modification and substitutions of the features and acts described can be made without departing from the intent and scope of the present invention. Accordingly, the invention is not to be considered as being limited by the foregoing description and drawings, but is only limited by the scope of the appended claims

What is claimed is:

1. A device for transferring a liquid medicament from a supply container to a flexible reservoir container, with a compartment unit and an adapter unit; wherein the compartment unit comprises a sealingly closable evacuation chamber, arranged for housing the flexible reservoir container and for being fluidly connected with a pump mechanism; and wherein the adapter unit comprises at least one transfer passage for transferring liquid from a supply container connected to the adapter unit to the flexible reservoir container, and a separator arranged in the transfer passage for separating gas bubbles from a liquid streaming through the transfer passage, the separator being fluidly connected to the chamber, wherein the separator comprises a liquid-impermeable, gas-permeable membrane that is on one side fluidly connected to the transfer passage and on the other side is fluidly connected to the chamber.

2. The device according to claim 1, wherein the separation of the gas bubbles from the liquid stream in the separator can be effected by a negative pressure in the chamber.

3. The device according to claim 1, wherein the separator comprises a liquid-permeable, hydrophilic membrane or a filter arranged in the transfer passage.

4. The device according to claim 1, wherein at least one of a main valve and a flow restrictor is arranged in the transfer passage upstream of the separator.

5. The device according to claim 4, wherein the device comprises the main valve arranged in the transfer passage upstream of the separator, and wherein the main valve is controlled by the pressure in the chamber.

6. The device according to claim 1, wherein the adapter unit is detachable and can be detachably secured and sealingly connected to the compartment unit.

7. The device according to claim 1, wherein the compartment unit comprises two casing parts that can be detachably secured to each other, thereby forming the sealingly closed chamber.

8. The device according to claim 7, wherein the adapter unit can be detachably secured to a casing part of the compartment unit.

9. The device according to claim 1, wherein a pump port or connector fluidly connects the chamber with the pump mechanism.

10. The device according to claim 1, wherein the flexible reservoir container is mounted in the chamber.

11. A kit comprising a device according to claim 1 and one or more flexible reservoir containers.

12. The kit according to claim 11, further comprising at least one of one or more casing parts in which a flexible reservoir container can be mounted, and one or more casing parts in which a flexible reservoir container is mounted.

13. A method for transferring a liquid medicament from a supply container to a flexible reservoir container, the method comprising:
   providing a fluid connection between the supply container and the flexible reservoir container;
   providing a separator arranged in the fluid connection for separating gas bubbles from the liquid;
   subjecting the flexible reservoir container to a reduced ambient pressure, thereby generating a negative pressure inside of the flexible reservoir container;
   sustaining normal ambient pressure inside of the supply container;
   subjecting the separator to the reduced ambient pressure, wherein the separation of the gas bubbles from the liquid in the separator is effected by the pressure difference between the liquid and the reduced ambient pressure; and
   conveying the liquid from the supply container to the flexible reservoir container, driven by the pressure difference between the inside of the supply container and the inside of the flexible reservoir container, wherein prior to filling the flexible reservoir container is evacuated via the separator, the separator being designed so that the flexible reservoir container is fluidly connected to its surroundings with its reduced ambient pressure as long as the separator has not yet come into contact with liquid.

14. The device according to claim 1, wherein the device comprises a venting valve fluidly connected to the chamber.

15. The device according to claim 1, wherein the compartment unit comprises two casing parts that can be detachably secured to each other, thereby forming the sealingly closed chamber, and wherein the adapter unit is detachable and can be detachably secured and sealingly connected to one of the casing parts.

16. The device according to claim 7, wherein one of the casing parts has a curved wall with a plurality of venting conduits.

17. The device according to claim 1, wherein the adapter unit comprises a connector part which connects with a corresponding connector part of the compartment unit.

18. The device according to claim 1, wherein the device comprises a main valve arranged in the transfer passage upstream of the separator, and wherein the main valve is a slide valve mechanism.

19. The device according to claim 1, wherein the adapter unit comprises a main valve arranged in the transfer passage upstream of the separator.

20. The device according to claim 1, wherein the adapter unit comprises a connector part which connects with a corresponding connector part of the compartment unit, and a main valve arranged in the transfer passage upstream of the separator, wherein the main valve is a slide valve mechanism.

* * * * *